United States Patent
Peleg et al.

(10) Patent No.: US 9,955,727 B2
(45) Date of Patent: May 1, 2018

(54) SOLID CORE ELECTRONIC CIGARETTE

(71) Applicant: Nu Mark Innovations Ltd., Beit Shemesh (IL)

(72) Inventors: Eyal Peleg, Tsoran (IL); Robert Levitz, North Miami Beach, FL (US); Shmuel Gavrielov, Jerusalem (IL); Sean Eastwood, Richmond, VA (US); Dorron Levy, Givatayim (IL)

(73) Assignee: Nu Mark Innovations Ltd., Beit Shemesh (IL)

( * ) Notice: Subject to any disclaimer, the term of this patent is extended or adjusted under 35 U.S.C. 154(b) by 787 days.

(21) Appl. No.: 14/335,394

(22) Filed: Jul. 18, 2014

(65) Prior Publication Data
US 2015/0027455 A1    Jan. 29, 2015

Related U.S. Application Data

(60) Provisional application No. 61/857,961, filed on Jul. 24, 2013.

(51) Int. Cl.
*A24F 47/00* (2006.01)
*A61M 15/06* (2006.01)

(52) U.S. Cl.
CPC ........... *A24F 47/008* (2013.01); *A61M 15/06* (2013.01)

(58) Field of Classification Search
CPC ...... A24F 47/008; A24F 47/006; A61M 15/06
See application file for complete search history.

(56) References Cited

U.S. PATENT DOCUMENTS

| | | | |
|---|---|---|---|
| 2004/0050383 A1* | 3/2004 | Cox | A61M 15/0003 128/200.14 |
| 2005/0172976 A1* | 8/2005 | Newman | A24F 47/008 131/194 |
| 2008/0092912 A1 | 4/2008 | Robinson et al. | |
| 2008/0268060 A1* | 10/2008 | Nguyen | A61K 9/0073 424/489 |
| 2010/0031968 A1 | 2/2010 | Sheikh et al. | |
| 2012/0111347 A1 | 5/2012 | Hon | |
| 2013/0074857 A1* | 3/2013 | Buchberger | A61M 15/06 131/329 |
| 2013/0160765 A1 | 6/2013 | Liu | |

(Continued)

FOREIGN PATENT DOCUMENTS

| CN | 1283326 C | 11/2006 |
|---|---|---|
| CN | 101557728 A | 10/2009 |

(Continued)

OTHER PUBLICATIONS

International Search Report and Written Opinion dated Mar. 2, 2015.

(Continued)

*Primary Examiner* — Jerzi H Moreno Hernandez
(74) *Attorney, Agent, or Firm* — Harness, Dickey & Pierce, P.L.C.

(57) ABSTRACT

An electronic cigarette comprises a battery portion that includes a battery which is operable to provide power to a heating element of the electronic cigarette, and a cartomizer coupled with the battery portion. The cartomizer comprises a solid core, and the heating element which vaporizes a portion of a liquefied portion of the solid core to form an aerosol mist that acts as a smoke replacement.

5 Claims, 5 Drawing Sheets

(56) References Cited

U.S. PATENT DOCUMENTS

| | | | |
|---|---|---|---|
| 2013/0167853 A1 | 7/2013 | Liu | |
| 2013/0220315 A1* | 8/2013 | Conley | A24F 47/008 128/202.21 |
| 2014/0000638 A1* | 1/2014 | Sebastian | A24F 47/008 131/328 |
| 2014/0123989 A1* | 5/2014 | LaMothe | A24F 47/008 131/328 |
| 2014/0190496 A1* | 7/2014 | Wensley | A24F 47/008 131/273 |
| 2014/0334802 A1* | 11/2014 | Dubief | A61L 9/03 392/390 |
| 2016/0021932 A1* | 1/2016 | Silvestrini | A24F 47/004 131/329 |

FOREIGN PATENT DOCUMENTS

| | | |
|---|---|---|
| CN | 201379072 Y | 1/2010 |
| EP | 2404515 A1 | 1/2012 |
| WO | WO-2013060743 A2 | 5/2013 |
| WO | WO-2013091251 A1 | 6/2013 |

OTHER PUBLICATIONS

An Office Action dated Nov. 11, 2017 issued in Eurasian Application No. 201690260 (PCT/IB2014/002417).
First Office Action dated Feb. 5, 2018 issued in Chinese Patent Application No. 201480051950.5.

\* cited by examiner ns disclosed herein. In the drawings, like referenced numerals designate corresponding parts throughout the different views.

SOLID CORE ELECTRONIC CIGARETTE

CROSS REFERENCE TO RELATED APPLICATION

This application claims priority under 35 U.S.C. § 119(e) to U.S. Provisional Application No. 61/857,961, filed on Jul. 24, 2013, the entire content of which is incorporated herein by reference thereto.

BACKGROUND

An electronic cigarette ("e-cigarette" or "e-Cig") is a device that emulates tobacco cigarette smoking by producing smoke replacement that may be similar in its physical sensation, general appearance, and sometimes flavor (i.e., with tobacco fragrance, menthol taste, added nicotine etc.) to that of tobacco cigarette smoke. A battery portion of the e-Cig includes a controller and a battery for powering the device and a cartomizer portion (i.e. aerosol mist generator) generates an aerosol mist (i.e. e-smoke or vapor) that is a replacement for cigarette smoke. In particular, the cartomizer may use heat, ultrasonic energy, or other means to vaporize a liquid solution (for example based on propylene glycol, or glycerin, for example including taste and fragrance ingredients) into an aerosol mist. The vaporization may be similar to nebulizer or humidifier vaporizing solutions for inhalation.

The vaporization process may occur with an e-Liquid. E-liquids may have a high viscosity at room temperature to enable longer shelf life and reduce leakages; however, this high viscosity may reduce the vaporization rate. A lower viscosity e-Liquid may have increased leakage or evaporation.

SUMMARY

Disclosed herein is an electronic cigarette which comprises a battery portion that includes a battery which is operable to provide power to a heating element of the electronic cigarette, and a cartomizer coupled with the battery portion. The cartomizer portion comprises a solid core, and the heating element which vaporizes a portion of a liquefied portion of the solid core to form an aerosol mist that acts as a smoke replacement.

Further disclosed herein is an electronic cigarette which comprises a battery portion that provides power to a heating element of the electronic cigarette, and a cartomizer coupled with the battery portion. The cartomizer comprises a solid core, wherein at least a portion of the solid core is configured to be transformed into a liquid; and the heating element that vaporizes the liquid to generate an aerosol mist.

Also disclosed herein is a method for electronic cigarette operation. The method comprises receiving, at the electronic cigarette, a puff of air, transforming, upon receipt of the air, at least a portion of a solid core into a liquid, and vaporizing the liquid to form an aerosol mist.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of the embodiments disclosed herein. In the drawings, like referenced numerals designate corresponding parts throughout the different views.

DETAILED DESCRIPTION

Figure 1:
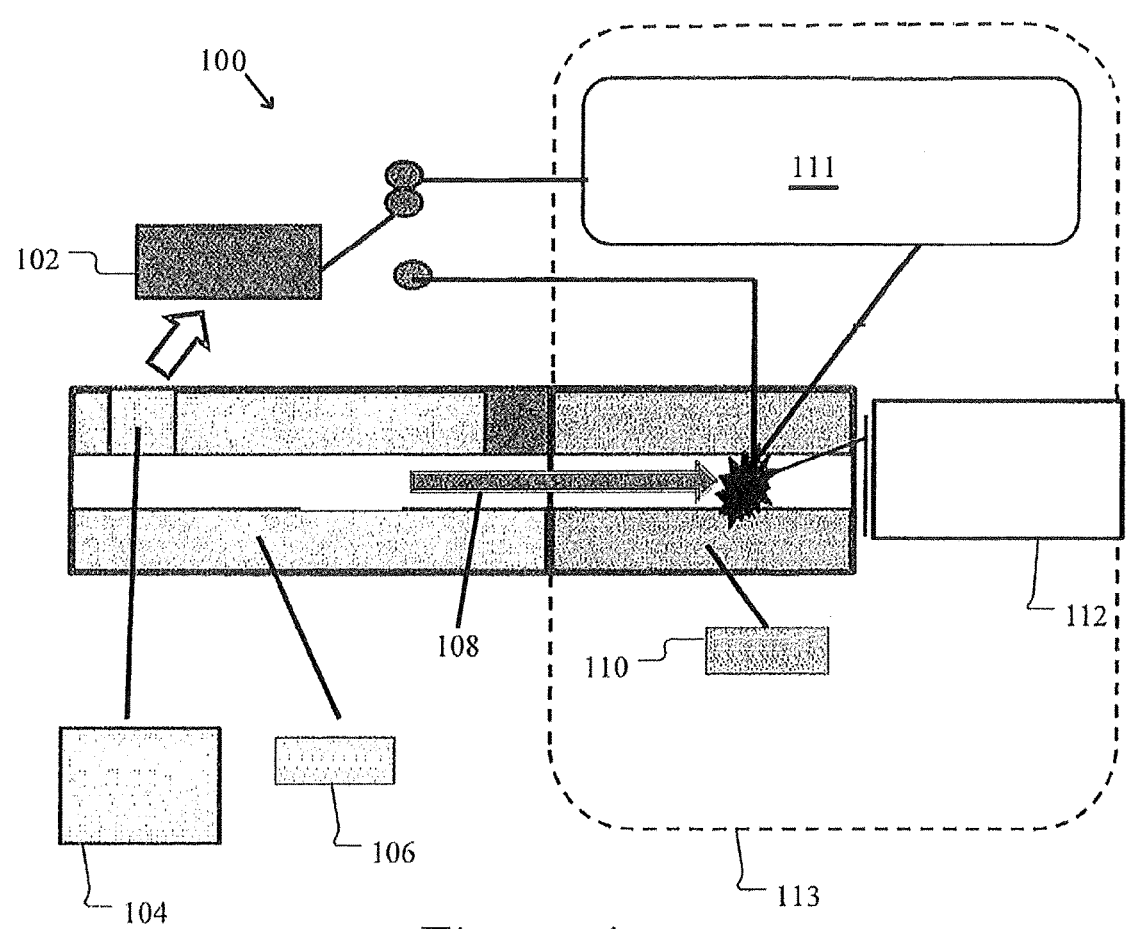
FIG. 1 is a diagram of an electronic cigarette.

By way of introduction, an e-Cig may include a solid core material as part of the cartomizer. The solid core can replace the liquid container (i.e. e-Liquid) from the cartomizer. In one embodiment, the solid material provides (holds) a fragrance or taste that is extracted from the solid core. In one embodiment, the solid core is transformed into a liquid and the liquid is then vaporized to generate a mist or e-smoke.

Other systems, methods, features and advantages will be, or will become, apparent to one with skill in the art upon examination of the following figures and detailed description. It is intended that all such additional systems, methods, features and advantages be included within this description, be within the scope of embodiments disclosed herein, and be protected by the following claims. Nothing in this section should be taken as a limitation on those claims. Further aspects and advantages are discussed below.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

FIG. 1 is a diagram of an electronic cigarette or electronic vaping device 100. The "smoke" produced by an e-Cig is a created by turning a core material 110 into mist and some vapor with an aerosol mist generator 112. Traditionally, the core material 110 was an e-Liquid stored in a liquid container; however, the core material 110 may be a solid according to the embodiments described herein. In one embodiment, the core material 110 may be a solid that is transformed into or generates a liquid (e.g. e-Liquid) that is used to generate a mist (aerosol) or smoke replacement. The cartomizer 113 may include the aerosol mist generator 112 and the core material 110. The cartomizer 113 may also be referred to as a cartridge throughout this disclosure and may be disposable. The core material 110 or e-Liquid is vaporized via air flow 108, generated by the inhalation of the user (i.e. the smoker or consumer or vapor), which produces a pressure difference that removes droplets from the core material 110. In one embodiment, the core material 110 may be part of a wick. In order to reduce the viscosity, to a level enabling vaporization, external heat may be applied through a heating element 111. The heating element 111 may be a coil in one embodiment that wraps around the wick in order to heat the liquid on the wick. Alternative embodiments for the vaporization process using the solid core 110 are further described below. Local viscosity may be reduced via heating, while inhalation occurs, enabling vaporization in the inhalation-generated flow of air 108. The core material 110 and/or e-Liquid formed from the core material 110 may be heated via an electric current flowing through the heating element 111 and may then be vaporized and evaporated through the e-Cig and may contain tastes and aromas that create a smoking sensation. A controller 102 may be activated due to air flow 108 (from the inhaled air) passing a flow sensor 104. The flow sensor 104 may be activated by a pressure drop across the flow sensor 104 and may directly switch battery 106 power on, or be used as an input for the controller 102 that then switches the battery 106 current on. Although illustrated as separate from the e-Cig, the controller 102 may be a part of the e-Cig (e.g. along with the battery 106). The battery 106 may be a separate/removable assembly. The battery 106 may include one or more electronic chips controlling and communicating from it. The battery 106 may connect with the cartomizer 113, which can be replaced or changed (e.g. when a new/different core material 110 is desired).

The e-Cig 100 may include two parts. The first part is often just referred to as the battery or battery portion (i.e. battery enclosure) and it includes the battery 106, the air flow sensor 104 and the controller 102. The second part is the cartridge (i.e. cartomizer 113) which includes the solid core material 110 and flavors that are required for smoke and flavor generation. The battery portion and the cartridge may be connected by metal connectors. An airflow tube of the battery enclosure and an airflow tube of the cartridge may enable the smoker to puff through the electronic cigarette and activate the flow sensor 104 inside the battery portion. This may trigger the controller 102 and cause the heating element 111 (e.g. coil) inside the cartridge to get hot, evaporate the e-Liquid that is in the cartridge and cause smoke (i.e. vapor). Although not shown in FIG. 1, the e-Cig 100 may include connections (i.e. connectors or electrical connections) that are used for power delivery to the heating element 11 land for charging the battery 106.

Figure 2:
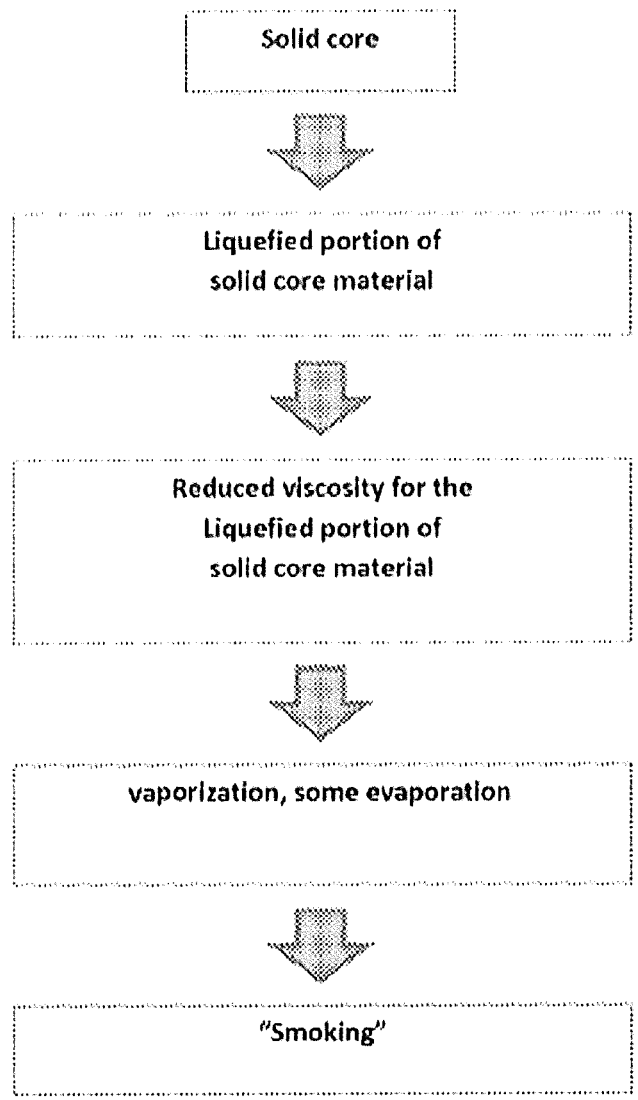
FIG. 2 is a flow chart for the operation of an electronic cigarette with a solid core.

FIG. 2 is a flow chart for the operation of an electronic cigarette with a solid core. The solid core may be a solid material or solid solution that holds a carrier (e.g. oil-based) fragrance and taste materials. Alternatively, other materials may also be held as part of the solid solution, such as nicotine. FIG. 2 illustrates a smoking process from a solid core. The solid core (or a small portion of the core) may be transformed into a liquid. If required, the viscosity of the liquid can be reduced during a viscosity-reducing stage (e.g., via application of heat). The liquefied portion of the solid core material will be vaporized (and maybe slightly vaporized) utilizing the inhalation air flow as part of the smoking process.

Figure 3:
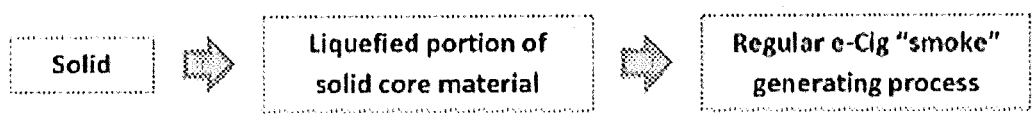
FIG. 3 is a flow chart for the simplified operation of an electronic cigarette with a solid core.

FIG. 3 is a flow chart for the simplified operation of an electronic cigarette with a solid core. In particular, FIG. 3 illustrates that at least a portion of the solid core is transformed into a liquid (i.e. the liquefied portion of the solid core material). From this point the traditional e-Cig process (for e-Liquids) may be performed for the vaporization to generate a mist or smoke replacement (e-smoke).

Other embodiments may include combinations of solid (for taste materials and other sensitive components) and a liquid (for example, a neutral liquid, such as water, to be used as a solvent). Alternatively, there may be a liquid held in a solid matrix, for example an open cell solid sponge. In one embodiment, the solid core may be subject to one or more of the following exemplary conditions: 1) the solid material should liquefy at attainable conditions inside an electronic cigarette (e.g. low temperature); 2) the material should be non-toxic, and should not create solid films or particles inside the human body; 3) the material viscosity, in working conditions, should fit vaporization processes as executed in and by the e-Cig; 4) the material should have sufficient shelf life (e.g., for months) in storage conditions (which may vary by design—e.g. the conditions may be room temperature, freezing conditions (similar to ice-cream), cool areas (similar to chocolate), or any other conditions set); 5) material conversion into liquid may or may not include latent heat (1st or 2nd order phase transition) and the material might be a super-cooled liquid at room temperature or in other conditions, the material may include components that upon release will vaporize, or go through sublimation process; and 6) the materials may be shapeable using standard manufacturing techniques, such as molding. These conditions are merely exemplary and there may be more or fewer conditions for the solid core. FIGS. 4-8 illustrate exemplary embodiments of an e-Cig with a solid core that may be subject to some of the conditions identified above.

Figure 4:
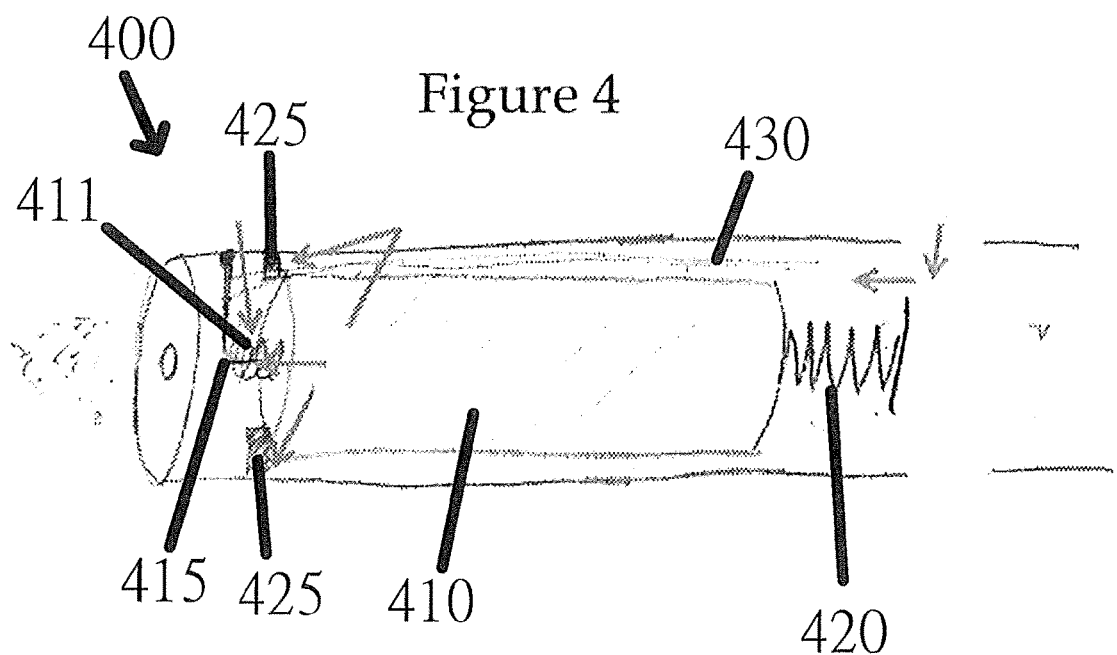
FIG. 4 is an embodiment of an electronic cigarette with a solid core.

FIG. 4 is an embodiment of an electronic cigarette 400 with a solid core 410. In this embodiment, a solid wick 415 touches the solid core 410, while a heating element 411 such as a heater coil liquefies a puddle of liquid at the position where the wick 415 touches the solid core 410. The puddle of liquid is absorbed by the wick 415, while airflow vaporizes some of the liquid, generating the mist or e-smoke. As the solid core 410 is consumed, it is pushed towards the wick 415 by a spring load (e.g. spring 420), up to stops 425. Electrical leads 430 may lead from the heating element 411 to the battery compartment, where the control systems may reside. Although not shown, the vaporization chamber may be designed to support vaporization of the liquid in and on the wick 415.

Figure 5:
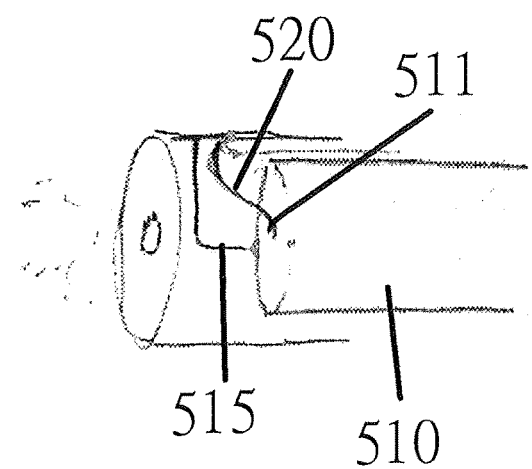
FIG. 5 is an embodiment of an electronic cigarette with a solid core and modified heating element.

FIG. 5 is an embodiment of an electronic cigarette 500 with a solid core 510 and modified heating element 511. In another embodiment, the heating coil may be replaced with a reed-like heating element 511, pressed via spring load (spring 520) to the point on the solid core 510 where a wick 515 touches the solid core 510. As the solid core 510 is solid, it may be constructed of layers, each with different taste, fragrance, or other property, to enrich the smoking experience. This may be utilized to generate various smoking experiences while the solid core 510 is consumed, for example to better imitate regular cigarettes smoking, which may differ in the beginning and the end of the regular cigarette.

In one embodiment, the solid core may be made out of ice. The e-Cig may be stored and used similarly to ice-cream. An advantage may be the ability to use water and water-soluble materials, so that the device may fit easily with certain health requirements. Another embodiment that may use water as the neutral liquid is shown in FIG. 6, with a solid core as the source for taste, fragrance and additive materials.

Figure 6:
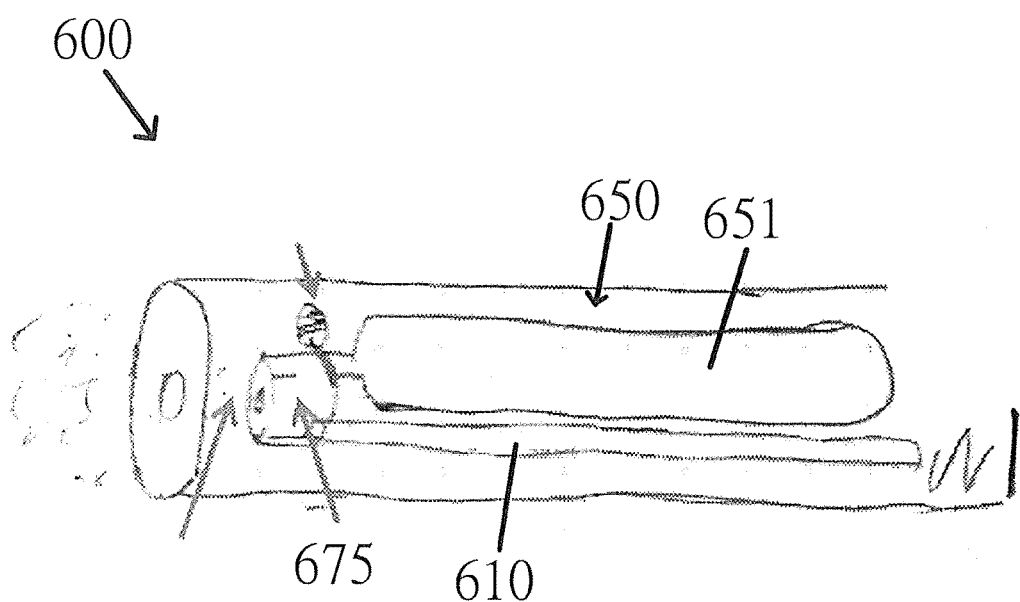
FIG. 6 is an embodiment of an electronic cigarette with a solid core and neutral liquid.

FIG. 6 is an embodiment of an electronic cigarette 600 with a solid core 610 and neutral liquid 650. Neutral liquid 650 is held in a container 651, and a portion of it is released into a mixing chamber 675, where the solid core 610 may touch the liquid 650 and dissolve into it. The liquid may be vaporized to become mist or e-smoke.

Figure 7:
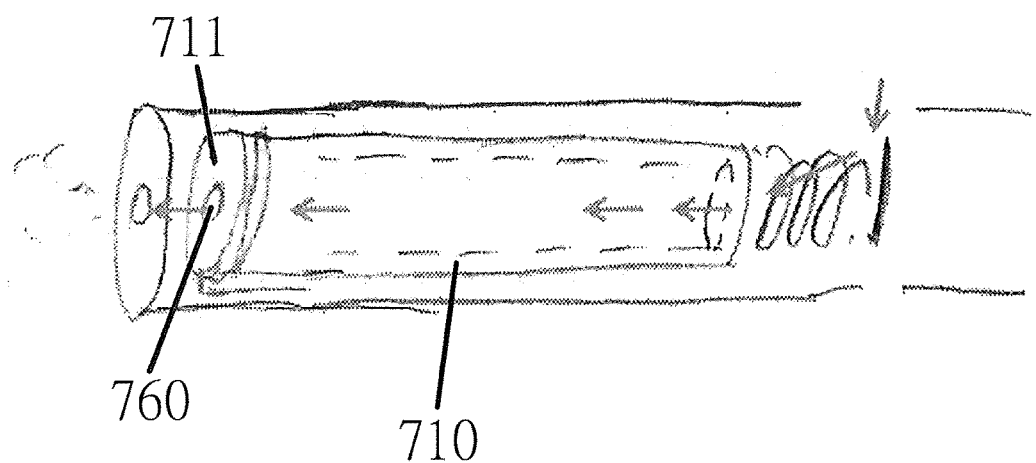
FIG. 7 is an embodiment of an electronic cigarette with a hollow core and disc shaped heating element.

FIG. 7 is an embodiment of an electronic cigarette 700 with a hollow core 710 and disc shaped heating element 711. In this embodiment, the solid core 710 may be made hollow, letting air flow in it. Heating for melting the solid core 710 can be applied via the disc shaped heating element 711 which is in a shape of a disk, with a hole 760 in its center. The air flow carries vaporized liquid to generate mist or e-smoke. This embodiment may have improved air flow characteristics, and better shape retention for the solid core 710.

Figure 8:
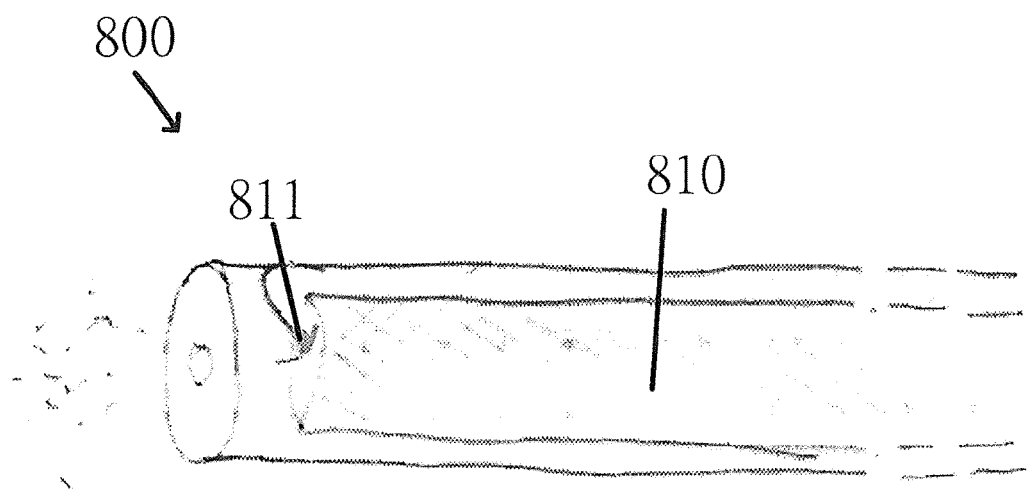
FIG. 8 is an embodiment of an electronic cigarette with a sponge core.

FIG. 8 is an embodiment of an electronic cigarette 800 with a sponge core 810. Other embodiments may employ different types of sponges, solid in the sense of shape retention, that release absorbed liquid via external impetus 811, such as heat or pressure or ultrasonic energy. The liquid is then vaporized using an appropriate flow structure (not shown) and the liquid is replenished by diffusion.

Another embodiment may position the solid core on the other side of the e-Cig, arranged in such a way that the e-Cig may shorten when the solid core is consumed. This, combined for example with an LED light source on the solid core tip, may more accurately imitate regular cigarettes.

A "computer-readable medium," "machine readable medium," "propagated signal" medium, and/or "signal-bearing medium" may comprise any device that includes, stores, communicates, propagates, or transports software for use by or in connection with an instruction executable system, apparatus, or device. The machine-readable medium may selectively be, but not limited to, an electronic, magnetic, optical, electromagnetic, infrared, or semiconductor system, apparatus, device, or propagation medium. A nonexhaustive list of examples of a machine-readable medium would include: an electrical connection "electronic" having one or more wires, a portable magnetic or optical disk, a volatile memory such as a Random Access Memory "RAM", a Read-Only Memory "ROM", an Erasable Programmable Read-Only Memory (EPROM or Flash memory), or an optical fiber. A machine-readable medium may also include a tangible medium upon which software is printed, as the software may be electronically stored as an image or in another format (e.g., through an optical scan), then compiled, and/or interpreted or otherwise processed. The processed medium may then be stored in a computer and/or machine memory.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

We claim:

1. A cartridge of an electronic vaping device comprising:
   a solid core,
   a heating element configured to vaporize a portion of a liquefied portion of the solid core to form a vapor; and
   a container configured to store water, the container configured to release a portion of the water into a mixing chamber, such that the solid core may contact the water and dissolve into the water to form the liquefied portion.

2. The cartridge of claim 1, wherein the cartridge further comprises a wick which contacts the liquefied portion, and wherein the heating element is configured to heat the portion of the liquefied portion which is absorbed by the wick before being vaporized to form the vapor.

3. The cartridge of claim 1, wherein the cartridge is disposable.

4. The cartridge of claim 1, wherein the heating element is a heater coil.

5. The cartridge of claim 4, wherein the heater coil is configured to generate the vapor by heating the portion of the liquefied portion.

* * * * *